US009260817B2

(12) United States Patent
Williams et al.

(10) Patent No.: US 9,260,817 B2
(45) Date of Patent: *Feb. 16, 2016

(54) FRESHENING COMPOSITIONS COMPRISING MALODOR BINDING POLYMERS AND MALODOR COUNTERACTANTS

(75) Inventors: Kristin Rhedrick Williams, West Chester, OH (US); Carla Jean Colina, Cincinnati, OH (US); Cahit Eylem, West Chester, OH (US); Lon Montgomery Gray, Florence, KY (US); Shih-Chuan Liou, Cincinnati, OH (US); Christine Marie Readnour, Fort Mitchell, KY (US); Ricky Ah-Man Woo, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 474 days.

This patent is subject to a terminal disclaimer.

(21) Appl. No.: 12/562,534

(22) Filed: Sep. 18, 2009

(65) Prior Publication Data

US 2011/0070181 A1    Mar. 24, 2011

(51) Int. Cl.
*A61L 9/01*          (2006.01)
*D06M 13/00*         (2006.01)
(Continued)

(52) U.S. Cl.
CPC .............. *D06M 13/005* (2013.01); *A61L 2/22* (2013.01); *A61L 9/01* (2013.01); *A61L 9/14* (2013.01);
(Continued)

(58) Field of Classification Search
CPC . A61L 9/012; A61L 2202/26; A61L 2209/13; A61L 2209/21; A61L 2/22; A61L 9/01; A61L 9/14; D06M 13/005; D06M 15/61; D06M 13/192; D06M 13/203; D06M 13/127; D06M 13/148; D06M 13/256; D06M 13/402; D06M 23/06; D06M 23/02; D06M 16/00
USPC .................................. 424/400, 76.1, 76.21
See application file for complete search history.

(56) References Cited

U.S. PATENT DOCUMENTS 5,578,563 A    11/1996 Trinh et al.
6,001,342 A    12/1999 Forestier et al.
(Continued)

FOREIGN PATENT DOCUMENTS

JP    WO 8201993    6/1982
JP    03146064      6/1991
(Continued)

OTHER PUBLICATIONS

"Methyl dihydrojasmonate" CASEN_24851-98-7; http://www.chemicalbook.com/CASEN_24851-98-7.htm.*
(Continued)

*Primary Examiner* — Sean Basquill
*Assistant Examiner* — Miriam A Levin
(74) *Attorney, Agent, or Firm* — Abbey A. Lopez; Amy I. Ahn-Roll (57) ABSTRACT

Freshening compositions comprising a malodor binding polymer, a malodor counteractant comprising at least one aliphatic aldehyde, and an aqueous carrier, wherein the composition is essentially free of any material that would soil or stain fabric; and methods thereof are provided. In some embodiments, the malodor binding polymer comprises a homopolymeric polyethylenimine having a molecular weight of about 1,000 to about 2,000,000. Such freshening compositions may be used to reduce malodor and/or microbes on inanimate surfaces or in the air.

15 Claims, 2 Drawing Sheets

(51) Int. Cl.

| | |
|---|---|
| *A61L 2/22* | (2006.01) |
| *A61L 9/14* | (2006.01) |
| *D06M 13/127* | (2006.01) |
| *D06M 13/148* | (2006.01) |
| *D06M 13/192* | (2006.01) |
| *D06M 13/203* | (2006.01) |
| *D06M 13/256* | (2006.01) |
| *D06M 13/402* | (2006.01) |
| *D06M 15/61* | (2006.01) |
| *D06M 23/02* | (2006.01) |
| *D06M 23/06* | (2006.01) |

(52) U.S. Cl.
CPC .......... *D06M 13/127* (2013.01); *D06M 13/148* (2013.01); *D06M 13/192* (2013.01); *D06M 13/203* (2013.01); *D06M 13/256* (2013.01); *D06M 13/402* (2013.01); *D06M 15/61* (2013.01); *D06M 23/02* (2013.01); *D06M 23/06* (2013.01); *A61L 2202/26* (2013.01); *A61L 2209/13* (2013.01); *A61L 2209/21* (2013.01)

(56) References Cited

U.S. PATENT DOCUMENTS

| | | | |
|---|---|---|---|
| 6,103,678 | A | 8/2000 | Masschelein et al. |
| 6,454,876 | B1 | 9/2002 | Ochomogo et al. |
| 6,653,274 | B1 | 11/2003 | Godfroid et al. |
| 6,680,289 | B1 | 1/2004 | Woo et al. |
| 6,833,342 | B2 | 12/2004 | Woo et al. |
| 7,998,403 | B2 | 8/2011 | Uchiyama et al. |
| 8,420,064 | B2 | 4/2013 | Takai et al. |
| 2002/0011584 | A1* | 1/2002 | Uchiyama et al. ........... 252/8.91 |
| 2003/0073607 | A1 | 4/2003 | Smets et al. |
| 2003/0228992 | A1* | 12/2003 | Smets et al. ................. 510/267 |
| 2009/0068138 | A1 | 3/2009 | Huang et al. |
| 2012/0183488 | A1* | 7/2012 | Woo et al. .................... 424/76.1 |

FOREIGN PATENT DOCUMENTS

| | | |
|---|---|---|
| JP | 2006149892 | 6/2006 |
| JP | 2007215831 | 8/2007 |
| JP | 2007 332130 A | 12/2007 |
| WO | WO 03/033636 A1 | 4/2003 |
| WO | WO 2005/108541 A1 | 11/2005 |

OTHER PUBLICATIONS

"(+)-Jasmonic acid, methyl ester (cis)-Compound Summary (CID 6427970)"; http://pubchem.ncbi.nlm.gov/summary/summary.cgi?=6427970&ncount=14.*

"Methyl phenyl carbinyl acetate—Compound Summary (CID 62341)"; http://pubchem.ncbi.nih.gov/summary/summary.cgi?cid=62341&n&ncount=41.*

"Santol pentenol" rw1032011; http://www.goodscentscompany.com/data/rw1032011.html.*

"Polysantol" 107898-54-4; http://www.guidechem.com/dictionary/107898-54-4.html.*

"Tetrahydropyran—ChemSpider ID 8554"; http://www.chemspider.com/Chemical-Structure.8554.html.*

"Rhubarb furan" rw1043021; http://www.thegoodscentscompany.com/data/rw1043021.html.*

Chempoint, BASF, Lupasol Polyethyleneimine [Retrieved from internet <URL: http://www.chempoint.com/products/catalog/basf/lupasol-polyethylenimine-adhesion-promoters/lupasol-polyethylenimine >], [Downloaded Jun. 28, 2015], 8 pages).*

Carytrad, BASF, Lupasol Types, Technical Information [Retrieved from internet <ULR: http://www.carytrad.com.tw/chemical/download/basf/08_0806130e_Lupasol%20types.pdf >], [Downloaded Jun. 28, 2015], 10 pages).*

Coussot et al., Colorimetric quantification of amino groups in linear and dendritic structures, Polym Int (2009), 58: 511-518 (published on-line Mar. 13, 2009), 8 pages.*

BASF, Care Chemicals & Formulators, Lupasol Types (Sep. 2010), 10 pages.*

U.S. Appl. No. 12/562,553, filed Sep. 18, 2009, Williams et al.

International Search Report dated Apr. 26, 2011, containing 5 pages.

Database WPI, Week 200809, Thomson Scientific, London, GB AN 2008-B34608 XP002631068.

* cited by examiner

FRESHENING COMPOSITIONS COMPRISING MALODOR BINDING POLYMERS AND MALODOR COUNTERACTANTS

FIELD OF THE INVENTION

The present invention relates to freshening compositions comprising a malodor binding polymer, malodor counteractants comprising at least one aliphatic aldehyde, and an aqueous carrier; and methods thereof.

BACKGROUND OF THE INVENTION

Freshening products for reducing or masking malodors on fabrics and in air are currently available and are described in the patent literature. The Procter & Gamble Company sells fabric and air freshening products under the FEBREZE® brand name. These products typically contain perfume, solubilizer, cyclodextrin, and an aqueous carrier. S.C. Johnson sells products such as Glade® Fabric and Air Odor Eliminator and Oust® Surface Disinfectant and Air Sanitizer. Reckitt-Benckiser sells products such as Lysol® Disinfectant Spray.

Certain freshening compositions do not effectively neutralize a broad range of malodors on fabrics and in the air. Further, certain freshening compositions may cause fabrics to turn yellow or brown under natural light and/or make fabric susceptible to soiling, particularly products that contain certain types or amounts of aldehydes and/or surfactants.

There remains a need for improved freshening compositions that neutralize a broad range of malodors, including malodors caused by microbes, and that provide a hedonic benefit, while avoiding soiling and staining of fabrics that may be contacted by the freshening composition.

SUMMARY OF THE INVENTION

The present invention relates to a freshening composition for reducing malodor. In one embodiment, the freshening composition for reducing malodor comprises an effective amount of a malodor binding polymer; a malodor counteractant comprising at least one aliphatic aldehyde; an aqueous carrier; wherein said composition is essentially free of any material that would soil or stain fabric. In another embodiment, the freshening composition comprises a homopolymeric polyethyleneimine having a molecular weight of 1,000 to 2,000,000; at least one aliphatic aldehyde; a glycol; a dicarboxylic acid to provide a pH of about 3 to about 8; about 90% to about 99.5% of an aqueous carrier; wherein said composition is essentially free of any material that would soil or stain fabric.

The present invention also relates to methods of reducing malodor comprising the steps of: providing a freshening composition comprising an effective amount of a malodor binding polymer, a malodor counteractant comprising at least one aliphatic aldehyde, an aqueous carrier, wherein said composition is essentially free of any material that would soil or stain fabric; and dispersing an effective amount of said freshening composition on an inanimate surface or in the air.

DETAILED DESCRIPTION OF THE INVENTION

The freshening composition of the present invention is designed to deliver genuine malodor reduction and not function merely by using perfume to cover up or mask odors. The freshening composition reduces malodor in the air or on inanimate surfaces, for example, fabrics that are contaminated with environmental odors such as food and tobacco odors, or wetted with perspiration. The freshening composition may also reduce microbes on inanimate surfaces or in air. The freshening composition may also act as a barrier to prevent malodors from adhering to or penetrating an inanimate surface.

A genuine malodor reduction provides a sensory and analytically measurable (e.g. gas chromatograph) malodor reduction. Thus, if the freshening composition delivers a genuine malodor reduction, the freshening composition will neutralize malodors in the air and/or on fabrics. "Neutralize" or "neutralization" as used herein means chemically reacting with malodor components (e.g. the reaction of primary amines with aldehydes to form imines, reductive alkylation of amines, protonation and deprotonation of amines, polymerization or de-polymerization); or suppressing the volatility of malodorous components such that other parts of the composition may react (e.g. acid-base neutralization); or physically entrapping odorous molecules such that they are not re-released into the air (e.g. cyclodextrin inclusion complexes as described herein).

I. Freshening Composition

The freshening composition for reducing malodor comprises a malodor binding polymer, a malodor counteractant comprising at least one aliphatic aldehyde, and an aqueous carrier, wherein said composition is essentially free of materials that soil or stain fabric. The total amount of surfactants (e.g. solubilizer, wetting agent) in the freshening composition is from 0% to 3% or no more than 3%, alternatively from 0% to 1% or no more than 1%, alternatively from 0% to 0.9% or no more than 0.9%, alternatively from 0% to 0.7 or no more than 0.7%, alternatively from 0% to 0.5% or no more than 0.5%, alternatively from 0% to 0.3% or no more than 0.3%, by weight of the composition. Compositions with higher concentrations can make fabrics susceptible to soiling and/or leave unacceptable visible stains on fabrics as the solution evaporates.

A. Malodor Binding Polymer

The freshening composition of the present invention includes a malodor binding polymer. A malodor binding polymer is polymer having an available functional group (e.g. amine) that has the affinity to neutralize malodor components. Monomers having an available function group with an affinity to neutralize malodor components are also contemplated. In the case of amine based compounds, the amine will have an affinity for aldehyde malodors. The amine may react with aldehyde malodors and form a new compound, such as an aminol, imine, or enamine which is not odorous.

A malodor binding polymer may include amine based compounds, such as monoamines, amino acids, polyethyleneimine polymers (PEIs), modified PEIs, substituted PEIs; acrylic acid polymers, such as polyacrylate co-polymer (e.g. Acumer™ 9000 from Rohm & Haas), polyacrylic acid polymers (e.g. Acusol™ from Rohm & Haas), and modified acrylate copolymers (e.g. Aculyn™ from Rohm & Haas); and modified methacrylate copolymers (e.g. HydroSal™ from Salvona Technologies); or mixtures thereof.

1. Amine Based Compounds

In some embodiments, the malodor binding polymer is an amine based compound with a molecular weight greater than 100 Daltons and at least 10% of its amine groups are primary amines. In one embodiment, the amine-based compound will be a polyamine with a molecular weight greater than 150 Daltons and 15% to 80% of its amine groups are primary amines. In another embodiment, the malodor binding polymer is an amine-based compound with a molecular weight greater than 1000 Daltons and from 0% to about 10% or less than 10% of its amine groups are primary amines.

A general structure for a primary amine compound useful in this invention is as follows:

B—(NH$_2$)$_n$;

wherein B is a carrier material, and n is an index of value of at least 1. Suitable B carriers include both inorganic and organic carrier moieties. By "inorganic carrier", it is meant a carrier which is comprised of non- or substantially non-carbon based backbones.

Compounds containing a secondary amine group have a structure similar to the above with the exception that the compound comprises one or more —NH— groups as well as —NH$_2$ groups. The amine compounds of this general type may be relatively viscous materials.

Exemplary amine based compounds are those selected from monoamines, aminoaryl derivatives, polyamines and derivatives thereof, polyamino acids and copolymers thereof, glucamines, dendrimers, PEIs, substituted amines and amides monoamines, or mixtures thereof.

a. Monoamines

Monoamines may be utilized in the present invention. Non-limiting examples of suitable monoamines for use in the present invention include, but are not limited to, primary amines that also contain hydroxy and/or alkoxy functional groups, such as the 2-hydroxyamines and/or 3-hydroxyamines; primary or secondary amines that also contain a functional group that enhances deposition of the monoamine compared to monoamines that lack that functional group, especially when the monoamine is interacting with the benefit agent. Primary monoamines may also be used herein in combination with secondary monoamines. However, sufficient levels of the primary monoamine must be used to provide at least 10% of the total amine groups within such combinations as primary amine groups.

b. Aminoaryl Derivatives

Exemplary aminoaryl derivatives are the amino-benzene derivatives including the alkyl esters of 4-amino benzoate compounds, ethyl-4-amino benzoate, phenylethyl-4-aminobenzoate, phenyl-4-aminobenzoate, 4-amino-N'-(3-aminopropyl)-benzamide, or mixtures thereof.

c. Polyamines

Examples of suitable amino functional polymers containing at least one primary amine group for the purposes of the present invention are:

Polyvinylamine with a MW of 300-2.10E6 Daltons (e.g Lupamine series 1500, 4500, 5000, 9000 available from BASF);

Polyvinylamine alkoxylated with a MW of ≥600 Daltons and a degree of ethoxylation of at least 0.5;

Polyvinylamine vinylalcohol-molar ratio 2:1, polyvinylaminevinylformamide-molar ratio 1:2 and polyvinylamine vinylformamide-molar ratio 2:1;

Triethylenetetramine, diethylenetriamine, tetraethylenepentamine;

Bis-aminopropylpiperazine;

amino substituted polyvinylalcohol with a MW ranging from 400-300,000 Daltons;

polyoxyethylene bis[amine] available from e.g. Sigma;

polyoxyethylene bis[6-aminohexyl] available from e.g. Sigma;

N,N'-bis-(3-aminopropyl)-1,3-propanediamine linear or branched (TPTA);

N,N'-bis-(3-aminopropyl)ethylenediamine;

bis(amino alkyl)alkyl diamine, linear or branched; and 1,4-bis-(3-aminopropyl)piperazine (BNPP).

d. Polyamino Acids

Suitable amine based compounds include polyamino acids. Polyamino acids are made up of amino acids or chemically modified amino acids. The amino acids may be selected from cysteine, histidine, isoleucine, tyrosine, tryptophane, leucine, lysine, glutamic acid, glutamine, glycine, alanine, aspartic acid, arginine, asparagine, phenylalanine, proline, serine, histidine, threonine, methionine, valine, and mixtures thereof. Amino acid derivatives may be tyrosine ethylate, glycine methylate, tryptophane ethylate, or mixtures thereof; homopolymers of amino acids; hydroxyamines; polyamino acids; or mixtures thereof.

In chemically modified amino acids, the amine or acidic function of the amino acid has reacted with a chemical reagent. This is often done to protect these chemical amine and acid functions of the amino acid in a subsequent reaction or to give special properties to the amino acids, like improved solubility. Examples of such chemical modifications are benzyloxycarbonyl, aminobutyric acid, butyl ester, and pyroglutamic acid. More examples of common modifications of amino acids and small amino acid fragments can be found in the Bachem, 1996, Peptides and Biochemicals Catalog.

One polyamino acid is polylysine, alternatively polylysines or polyamino acids where more than 50% of the amino acids are lysine, since the primary amine function in the side chain of the lysine is the most reactive amine of all amino acids. One polyamino acid has a molecular weight of 500 to 10,000,000, alternatively between 2000 and 25,000.

The polyamino acid can be cross linked. The cross linking can be obtained for example by condensation of the amine group in the side chain of the amino acid like lysine with the carboxyl function on the amino acid or with protein cross linkers like PEG derivatives. The cross linked polyamino acids still need to have free primary and/or secondary amino groups left for neutralization. Cross linked polyamino acid has a molecular weight of 20,000 to 10,000,000; alternatively between 200,000 and 2,000,000.

The polyamino acid or the amino acid can be co-polymerized with other reagents like for instance with acids, amides, acyl chlorides, aminocaproic acid, adipic acid, ethylhexanoic acid, caprolactam, or mixtures thereof. The molar ratio used in these copolymers ranges from 1:1 (reagent/amino acid (lysine)) to 1:20, alternatively from 1:1 to 1:10. The polyamino acid like polylysine can be unethoxylated or partially ethoxylated so long as the requisite amount of primary amine remains in the polymer.

e. Dendrimers

Also useful amine based compounds are polypropylenimine dendrimers and the commercially available Starburst® polyamidoamines (PAMAM) dendrimers, generation G0-G10 from Dendritech and the dendrimers Astromols®, generation 1-5 from DSM being DiAminoButane PolyAmine DAB (PA)x dendrimers with x=2$^n$×4 and n being generally comprised between 0 and 4.

f. PEIs

In one embodiment, the malodor binding polymer is a PEI. It has been surprisingly discovered that amine based polymers at a pH of about 4 to about 8, alternatively above 5 to about 8, alternatively 7 can neutralize amine based odors. PEIs have the following general formula:

—(CH2-CH2-NH)$n$-; $n$=10-10$_5$

Homopolymeric PEIs are branched, spherical polyamines with a well defined ratio of primary, secondary and tertiary amine functions. They are best described in the following partial structural formula:

The chemical structure of homopolymeric PEIs follows a simple principle: one amine function—two carbons.

The freshening composition may comprise a homopolymeric polyethylenimine having a molecular weight of about 800 to about 2,000,000, alternatively about 1,000 to about 2,000,000, alternatively about 1,200 to about 25,000, alternatively about 1,300 to about 25,000, alternatively about 2,000 to about 25,000, alternatively about 10,000 to about 2,000,000, alternatively about 25,000 to about 2,000,000, alternatively about 25,000. The freshening composition may comprise a homopolymeric polyethylenimine having 15% to 80% primary amino groups. Exemplary homopolymeric PEIs include those that are commercially available under the tradename LUPASOL® from BASF. Lupasol products are usually obtained through polymerization of the ethylenimine monomer. The ethylenimine monomer has totally reacted in the polymer matrix. Suitable LUPASOL® products include LUPASOL® FG (MW 800; 42% primary amines), G20wf (MW 1300; 40% primary amines), PR8515 (MW 2000; 40% primary amines), WF (MW 25,000; 36% primary amines), FC (MW 800), G20 (MW 1300; 40% primary amines), G35 (MW 2000; 38% primary amines), G100 (MW 2-0005000; 37% primary amines), HF (MW 25,000; 36% primary amines), P (MW 750,000; 37% primary amines), PS (MW 750,000; 37% primary amines), SK (MW 2,000,000), SNA (MW 1,000,000). Technical information the LUPASOL® products can be found in "Lupasol Types", BASF, Care Chemicals & Formulators, September 2010. The molecular weight of LUPASOL® products are recorded as an average molar mass in g/mol (GPC, BASF method).

In some embodiments, the freshening composition comprises Lupasol HF or WF (MW 25,000), P (MW 750,000), PS (MW 750,000), SK (MW 2,000,000), G20wfv (MW 1300) or PR 1815 (MW 2000), or Epomin SP-103, Epomin SP-110, Epomin SP-003, Epomin SP-006, Epomin SP-012, Epomin SP-018, Epomin SP-200, or partially alkoxylated polyethyleneimine, like polyethyleneimine 80% ethoxylated from Aldrich. In one embodiment, the freshening composition contains Lupasol WF (MW 25,000).

Also suitable amine based compounds for use in the freshening composition are modified PEIs, partially alkylated polyethylene polymers, PEIs with hydroxyl groups, 1,5-pentanediamine, 1,6-hexanediamine, 1,3 pentanediamine, 3-dimethylpropanediamine, 1,2-cyclohexanediamine, 1,3-bis(aminomethyl)cyclohexane, tripropylenetetraamine, bis(3-aminopropyl)piperazine, dipropylenetriamine, tris(2-aminoethylamine), tetraethylenepentamine, bishexamethylenetriamine, bis(3-aminopropyl) 1,6-hexamethylenediamine, 3,3'-diamino-N-methyldipropylamine, 2-methyl-1,5-pentanediamine, N,N,N',N'-tetra(2-aminoethyl)ethylenediamine, N,N,N',N'-tetra(3-aminopropyl)-1,4-butanediamine, pentaethylhexamine, 1,3-diamino-2-propyl-tert-butylether, isophorondiamine, 4,4',-diaminodicyclohylmethane, N-methyl-N-(3-aminopropyl)ethanolamine, spermine, spermidine, 1-piperazineethaneamine, 2-(bis(2-aminoethyl)amino)ethanol, ethoxylated N-(tallowalkyl)trimethylene diamines,poly[oxy(methyl-1,2-ethanediyl)], α-(2-aminomethylethoxy)-(=C.A.S No. 9046-10-0); poly[oxy(methyl-1,2-ethanediyl)], α-hydro-)-ω-(2-aminomethylethoxy)-, ether with 2-ethyl-2-(hydroxymethyl)-1,3-propanediol (=C.A.S, No. 39423-51-3); commercially available under the tradename Jeffamines T-403, D-230, D-400, D-2000; 2,2',2"-triaminotriethylamine; 2,2'-diamino-diethylamine; 3,3'-diamino-dipropylamine, 1,3 bis aminoethyl-cyclohexane commercially available from Mitsubishi, and the C12 Sternamines commercially available from Clariant like the C12 Sternamin(propylenamine)$_n$ with n=¾.

In one embodiment, the malodor binding polymer may be used in an effective amount to provide a reduction of microbes on fabric and/or in the air. When using a malodor binding polymer, an effective amount reduces microbes by at least 1 log difference as compared to a composition lacking the malodor binding polymer. This difference is then attributed to the use of the malodor binding polymer and not the inherent variability in the microbial species.

Suitable levels of malodor binding polymer are from about 0.01% to about 2%, alternatively from about 0.01% to about 1%, alternatively about 0.01% to about 0.8%, alternatively about 0.01% to about 0.6%, alternatively about 0.01% to about 0.1%, alternatively about 0.01% to about 0.07%, alternatively about 0.07%, by weight of the freshening composition. Compositions with higher amount of malodor binding polymer may make fabrics susceptible to soiling and/or leave unacceptable visible stains on fabrics as the solution evaporates off of the fabric.

B. Malodor Counteractants

The freshening composition may utilize one or more malodor counteractants. Malodor counteractants may include components which lower the vapor pressure of odorous compounds, solubilize malodor compounds, physically entrap odors (e.g. flocculate or encapsulate), physically bind odors, or physically repel odors from binding to inanimate surfaces. For example, aliphatic aldehydes react with amine odors, such as fish and cigarette odors. When used in combination with the malodor binding polymer, the freshening composition may neutralize a broader range of malodor causing materials which, in turn, further reduces malodors in the air or on inanimate surfaces.

1. Aliphatic Aldehydes

In one embodiment, the freshening composition comprises a perfume mixture having one or more fabric-safe, non-yellowing aliphatic aldehydes. Certain types of aldehydes that predominately comprise a straight chain aliphatic backbone will not discolor fabrics, unlike products that utilize types of aldehydes that contain multiple double bonds and benzene rings. The following table illustrates the selection of aldehydes to avoid fabric yellowing.

| AldehydeSolution Tested | Fadometer Test on treated Fabric (0.75 grams of product are pipetted onto a 4 inch × 4 inch (10 cm × 10 cm) swatch which is then subjected to 5 hours of exposure to simulated sunlight using a SUNTEST CPS+ model Fadometer supplied by Atlas, Chicago, Illinois, USA. |
|---|---|
| Control- untreated fabric swatch | No yellowing |
| 1000 ppm amylic cinnamic aldehyde (aromatic) | Yellowish brown |
| 1000 ppm citronellal (aromatic) | Yellowish brown |
| 1000 ppm citral aldehyde (aliphatic) | No yellowing |
| 1000 ppm lauric aldehyde (aliphatic) | No yellowing |

Examples of suitable aliphatic aldehydes are R—COH where R is saturated $C_7$ to $C_{22}$ linear and/or branched with no more than two double bonds. Examples of suitable aliphatic aldehydes are bourgeonal, citral, citronellyl oxyacetaldehyde, cymal, decyl aldehyde, helional, hexyl cinnamic aldehyde, lauric aldehyde, ligustral, lyral, melonal, [methyl dihydro jasmonate], methyl nonyl acetaldehyde, [methyl phenyl carbinyl acetate], nonyl aldehyde, octyl aldehyde, [oxane], P. T. bucinal, [polysantol], [rhubafuran], tripal, or mixtures thereof.

In one embodiment, the freshening composition includes at least one aliphatic aldehyde selected from the group consisting of: bourgeonal, citral, citronellyl oxyacetaldehyde, cymal, decyl aldehyde, helional, hexyl cinnamic aldehyde, lauric aldehyde, ligustral, lyral, melonal, [methyl dihydro jasmonate], methyl nonyl acetaldehyde, [methyl phenyl carbinyl acetate], nonyl aldehyde, 2,6-nonadien-1-al, octyl aldehyde, [oxane], P.T. bucinal, [polysantol], [rhubafuran], tripal, and mixtures thereof.

In another embodiment, the freshening composition includes at least one aliphatic aldehyde selected from the group consisting of: bourgeonal, cymal, hexyl cinnamic aldehyde, [mmethyl dihydro jasmonate], methyl nonyl acetaldehyde, P.T. bucinal, and mixtures therof.

In addition to the aforementioned aliphatic aldehydes, any one or more of the following materials may be added to the at least one aliphatic aldehyde: methyl dihydro jasmonate (an ester), methyl phenyl carbinyl acetate (an ester), oxane (a tetrahydropyran), polysantol (an alcohol), and rhubafuran (a tetrahydropyran), and mixtures thereof. For purposes of the present invention, methyl dihydro jasmonate, methyl phenyl carbinyl acetate, oxane, polysantol, and rhubafuran are referred to as aliphatic aldehydes rather than referring to each of these materials individually.

The aliphatic aldehydes may be present in an amount from about 0.001% to about 10%, alternatively from about 0.001% to about 5%, alternatively from about 0.01% to about 1%, alternatively from about 0.02% to about 1%, alternatively from about 0.02% to about 0.5%, alternatively from about 0.02% to about 0.06%, alternatively about 0.06%, by weight of the freshening composition.

In addition to aliphatic aldehydes, the freshening composition may also include perfume materials for their scent experience including enones, ketones, ionones including ionone alpha, ionone beta, ionone gamma methyl, or mixtures thereof. Suitable perfume materials are discussed in U.S. Pat. No. 5,714,137. The freshening composition may contain an effective amount of perfume to provide the freshening fragrance when first sprayed, some lingering fragrance, and some extra fragrance to be released upon fabric rewetting. It may be desirable for the aliphatic aldehydes to have virtually no negative impact on the desired perfume character.

Certain malodor counteractants may be odoriferous and negatively impact the overall character of the fragrance. In this case, a perfume/malodor counteractant premix is formed such that the perfume raw materials used are selected to neutralize any odor of the malodor counteractants. This odor neutralized premix can then be added to a parent perfume mixture without affecting the character of the parent fragrance. This permits the malodor counteractants to be used broadly with a large variety of fragrance types.

The following are non-limiting examples of perfume formulations that include fabric-safe malodor counteractants.

(1) Pine

| Material Name | Amount |
|---|---|
| Rosemary | 10.00 |
| Spike Lavender | 10.00 |
| Lavandin Grosso | 5.00 |
| Spruce (conf.-manh) | 5.00 |
| Camphor Gum | 5.00 |
| Melonal | 0.30 |
| Eucalyptol | 15.00 |
| Iso Menthone | 15.00 |
| Iso Bornyl Acetate | 21.70 |
| Ionone Beta | 8.00 |
| Iso E Super | 5.00 |
| | 100.00 |

(2) Ozonic

| Material Name | Amount |
|---|---|
| Xi Aldehyde | 8.00 |
| 2'6 Nonadienol 10% In Dpg | 5.00 |
| Helional | 13.00 |
| Hydroxycitronellal | 11.50 |
| Calone 1951 | 0.50 |
| 2'6-Nonadien-1-al/10% In Dpg | 5.00 |
| Lyral | 20.00 |
| Melonal | 1.00 |
| Iso Menthone | 10.00 |
| Floralozone | 10.00 |
| Bourgeonal | 10.00 |
| Delta Muscenone 962191 | 1.00 |
| Habanolide 100% | 5.00 |
| | 100.00 |

(3) Fruity

| Material Name | Amount |
|---|---|
| Fruitate | 5.00 |
| Orange Terpenes | 13.00 |
| Ethyl Acetoacetate | 3.00 |

-continued

| Material Name | Amount |
| --- | --- |
| 2'6 Nonadienol 10% In Dpg | 1.00 |
| Ethyl Acetate | 3.00 |
| Benzaldehyde | 2.00 |
| Prenyl Acetate | 8.00 |
| Benzyl Acetate | 15.00 |
| 2' 6-Nonadien-1-al/10% In Dpg | 1.00 |
| Ethyl-2-methyl Butyrate | 8.00 |
| Amyl Acetate | 3.00 |
| Cis 3 Hexenyl Acetate | 3.00 |
| Methyl Dihydro Jasmonate | 10.00 |
| Ligustral | 5.00 |
| Melonal | 1.00 |
| Ethyl 2 Methyl Pentanoate | 8.00 |
| Hexyl Acetate | 8.00 |
| Habanolide 100% | 3.00 |
| | 100.00 |

(4) Citrus

| Material Name | Amount |
| --- | --- |
| Orange Terpenes | 20.00 |
| Lemon Terpenes X5 Fold | 20.00 |
| Lime Oil Cf-8-1285-1 (conf.-berje) | 10.00 |
| Grapefruit Phase C-Ref. N*12245 | 20.00 |
| Italian Orange Phase Oil | 22.90 |
| Delta Muscenone 962191 | 0.50 |
| Oxane | 0.30 |
| Iso Menthone | 1.00 |
| Rhubafuran | 0.30 |
| Habanolide 100% | 5.00 |
| | 100.00 |

(5) Floral

| Material Name | Amount |
| --- | --- |
| Spike Lavender | 5.00 |
| Rosemary | 5.00 |
| Helional | 10.00 |
| Hydroxycitronellal | 10.00 |
| Benzyl Acetate | 9.30 |
| Lyral | 20.00 |
| Ligustral | 2.00 |
| Melonal | 0.20 |
| Eucalyptol | 2.00 |
| Iso Menthone | 8.00 |
| Bourgeonal | 20.00 |
| Undecavertol | 3.00 |
| Delta Muscenone 962191 | 0.50 |
| Habanolide 100% | 5.00 |
| | 100.00 |

In certain cases, fabrics that are laundered will have residual brighteners deposited from detergents with which they are washed. Therefore, it may be desirable for the aliphatic aldehydes to be compatible with brighteners so that the freshening composition will not discolor any fabrics with which it comes into contact. A number of the examples above are compatible with brighteners.

2. Low Molecular Weight Polyols

Low molecular weight polyols with relatively high boiling points, as compared to water, such as ethylene glycol, diethylene glycol, triethylene glycol, propylene glycol, dipropylene glycol, and/or glycerine may be utilized as a malodor counteractant for improving odor neutralization of the freshening composition of the present invention. Some polyols, e.g., dipropylene glycol, are also useful to facilitate the solubilization of some perfume ingredients in the composition of the present invention.

The glycol used in the freshening composition of the present invention may be glycerine, ethylene glycol, propylene glycol, dipropylene glycol, polyethylene glycol, propylene glycol methyl ether, propylene glycol phenyl ether, propylene glycol methyl ether acetate, propylene glycol n-butyl ether, dipropylene glycol n-butyl ether, dipropylene glycol n-propyl ether, ethylene glycol phenyl ether, diethylene glycol n-butyl ether, dipropylene glycol n-butyl ether, diethylene glycol mono butyl ether, dipropylene glycol methyl ether, tripropylene glycol methyl ether, tripropylene glycol n-butyl ether, other glycol ethers, or mixtures thereof. In one embodiment, the glycol used is ethylene glycol, propylene glycol, or mixtures thereof. In another embodiment, the glycol used is diethylene glycol.

Typically, the low molecular weight polyol is added to the composition of the present invention at a level of from about 0.01% to about 5%, by weight of the composition, alternatively from about 0.05% to about 1%, alternatively from about 0.1% to about 0.5%, by weight of the composition. Compositions with higher concentrations may make fabrics susceptible to soiling and/or leave unacceptable visible stains on fabrics as the solution evaporates off of the fabric. The weight ratio of low molecular weight polyol to the malodor binding polymer is from about 500:1 to about 4:1, alternatively from about 1:100 to about 25:1, alternatively from about 1:50 to about 4:1, alternatively about 4:1.

3. Cyclodextrin

In some embodiments, the freshening composition may include solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. No. 5,714,137, and U.S. Pat. No. 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the freshening composition. Freshening compositions with higher concentrations can make fabrics susceptible to soiling and/or leave unacceptable visible stains on fabrics as the solution evaporates off of the fabric. The latter is especially a problem on thin, colored, synthetic fabrics. In order to avoid or minimize the occurrence of fabric staining, the fabric may be treated at a level of less than about 5 mg of cyclodextrin per mg of fabric, alternatively less than about 2 mg of cyclodextrin per mg of fabric.

C. Buffering Agent

The freshening composition of the present invention includes a buffering agent which may be a dibasic acid, carboxylic acid, or a dicarboxylic acid like maleic acid. The acid may be sterically stable, and used in this composition solely for maintaining the desired pH. The freshening composition may have a pH from about 3 to about 8, alternatively from about 4 to about 7, alternatively from about 5 to about 8, alternatively from about 6 to about 8, alternatively about 6 to about 7, alternatively about 7, alternatively about 6.5.

Carboxylic acids such as citric acid may act as metal ion chelants and can form metallic salts with low water solubility. As such, in some embodiments, the freshening composition is essentially free of citric acids. The buffer can be alkaline, acidic or neutral.

Other suitable buffering agents for freshening compositions of this invention include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl)amino methane ($HOCH_2$)$_3CNH_3$ (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl)methyl glycine (tricine). Mixtures of any of the above are also acceptable.

The freshening compositions may contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

D. Solubilizer

The freshening composition of the present invention may contain a solubilizing aid to solubilize any excess hydrophobic organic materials, particularly any perfume materials, and also optional ingredients (e.g., insect repelling agent, antioxidant, etc.) which can be added to the composition, that are not readily soluble in the composition, to form a clear solution. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

In some embodiments, the freshening composition contains nonionic surfactants, cationic surfactants, and mixtures thereof. In one embodiment, the freshening composition contains hydrogenated castor oil. One suitable hydrogenated castor oil that may be used in the present composition is Basophor™, available from BASF.

Compositions containing anionic surfactants and/or detergent surfactants may make fabrics susceptible to soiling and/or leave unacceptable visible stains on fabrics as the solution evaporates off of the fabric. In some embodiments, the freshening composition is free of anionic surfactants and/or detergent surfactants.

When the solubilizing agent is present, it is typically present at a level of from about 0.01% to about 3%, alternatively from about 0.05% to about 1%, alternatively from about 0.01% to about 0.05%, by weight of the freshening composition. Freshening compositions with higher concentrations may make fabrics susceptible to soiling and/or leave unacceptable visible stains on fabrics as the solution evaporates off of the fabric.

E. Antimicrobial Compounds

The freshening composition of the present invention may include an effective amount of a compound for reducing microbes in the air or on inanimate surfaces. Antimicrobial compounds are effective on gram negative and gram positive bacteria and fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Steptococcus pyogenes, Salmonella choleraesuis, Escherichia coli, Trichophyton mentagrophytes*, and *Pseudomonoas aeruginosa*. In some embodiments, the antimicrobial compounds are also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the freshening composition of the present invention can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

In one embodiment, a quaternary compound is used. Examples of commercially available quaternary compounds suitable for use in the freshening composition is Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the freshening composition.

F. Preservatives

The freshening composition of the present invention may include a preservative. The preservative is included in the present invention in an amount sufficient to prevent spoilage or prevent growth of inadvertently added microorganisms for a specific period of time, but not sufficient enough to contribute to the odor neutralizing performance of the freshening composition. In other words, the preservative is not being used as the antimicrobial compound to kill microorganisms on the surface onto which the composition is deposited in order to eliminate odors produced by microorganisms. Instead, it is being used to prevent spoilage of the freshening composition in order to increase the shelf-life of the composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives for use in the present invention include a mixture of about 77% 5-chloro-2-methyl-4-isothiazolin-3- one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative are from about 0.0001% to about 0.5%, alternatively from about 0.0002% to about 0.2%, alternatively from about 0.0003% to about 0.1%, by weight of the freshening composition.

G. Wetting Agent

The freshening composition may include a wetting agent that provides a low surface tension that permits the composition to spread readily and more uniformly on hydrophobic surfaces like polyester and nylon. It has been found that the aqueous solution, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated aqueous compositions.

Nonlimiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of cyclodextrin-compatible wetting agents of this type are described in U.S. Pat. No. 5,714,137 and include the Silwet® surfactants available from Momentive Performance Chemical, Albany, N.Y. Exemplary Silwet surfactants are as follows:

| Name | Average MW |
|---|---|
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |
| L-7602 | 3,000; | and mixtures thereof.

H. Aqueous Carrier

The freshening composition of the present invention may include an aqueous carrier. The aqueous carrier which is used may be distilled, deionized, or tap water. Water may be present in any amount for the composition to be an aqueous solution. In some embodiments, water may be present in an amount of about 85% to 99.5%, alternatively about 90% to about 99.5%, alternatively about 92% to about 99.5%, alternatively about 95%, by weight of said freshening composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, the level of monohydric alcohol may be less than about 6%, alternatively less than about 3%, alternatively less than about 1%, by weight of the freshening composition.

I. Other Optional Ingredients

Adjuvants can be optionally added to the freshening composition herein for their known purposes. Such adjuvants include, but are not limited to, water soluble metallic salts, antistatic agents, insect and moth repelling agents, colorants, antioxidants, and mixtures thereof.

II. Method of Making

The freshening composition can be made in any suitable manner known in the art. All of the ingredients can simply be mixed together. In certain embodiments, it may be desirable to make a concentrated mixture of ingredients and dilute by adding the same to an aqueous carrier before dispersing the composition into the air or on an inanimate surface. In another embodiment, the malodor binding polymer may be dispersed in one vessel containing deionized water and ethanol, and low molecular polyols. To this vessel, then, the buffer is added until fully dispersed and visually dissolved. In a separate vessel, the solubilizer and perfume are mixed until homogenous. The solution of solubilizer and perfume are then added to the first mixing vessel, and mixed until homogenous.

III. Methods of Use

The freshening composition of the present invention can be used by dispersing, e.g., by placing the aqueous solution into a dispensing means, such as a spray dispenser and spraying an effective amount into the air or onto the desired surface or article. An effective amount as defined herein means an amount sufficient to neutralize malodor to the point that it is not discernible by the human sense of smell yet not so much as to saturate or create a pool of liquid on an article or surface and so that, when dry, there is no visual deposit readily discernible. Dispersing can be achieved by using a spray device, a roller, a pad, etc.

The present invention encompasses the method of dispersing an effective amount of the composition for reducing malodor onto household surfaces. The household surfaces are selected from the group consisting of countertops, cabinets, walls, floors, bathroom surfaces, and kitchen surfaces.

The present invention encompasses the method of dispersing a mist of an effective amount of the composition for reducing malodor onto fabric and/or fabric articles. The fabric and/or fabric articles include, but are not limited to, clothes, curtains, drapes, upholstered furniture, carpeting, bed linens, bath linens, tablecloths, sleeping bags, tents, car interior, e.g., car carpet, fabric car seats, etc.

The present invention relates to the method of dispersing a mist of an effective amount of the composition for reducing malodor impression onto cat litter, pet bedding and pet houses to neutralize malodor.

The present invention relates to the method of dispersing a mist of an effective amount of the composition for reducing malodor impression onto household pets to neutralize malodor.

EXAMPLES

Malodor Reduction

Table 1 show non-limiting examples of freshening compositions according to the present invention.

TABLE 1

|  | I | II | III | IV | V (Control) | VI | VII | VIII |
|---|---|---|---|---|---|---|---|---|
| LUPASOL ™ WF CAS 9002-98-6 | 0.070 | 0.070 | 0.015 | 0.035 | 0 | 0.035 | 0.0525 | 0.07 |
| Diethylene Glycol | 0.175 | 0.175 | 0.070 | 0.175 | 0.175 | 0.175 | 0.170 | 0.175 |
| Perfume mixture comprising aliphatic aldehydes | 0.2102 | 0.4880 | 0.020 (0% aldehydes) | 0.236 | 0.655 (0.012 aldehydes) | 0.655 (0.012 aldehydes) | 0.655 (0.012 aldehydes) | 0.655 (0.012 aldehydes) |
| Hydroxypropyl Beta Cyclodextrin (CD) | 0.630 | 0.630 | 0.630 | 0 | 0.630 | 0.630 | 0.630 | 0.630 |
| BASOPHOR ™ ELH 60 | 0 | 0.050 | 0.050 | 0.050 | 0.050 | 0.050 | 0.050 | 0.050 |
| UNIQUAT ™ 2250 | 0 | 0.060 | 0 | 0.060 | 0.060 | 0.060 | 0.060 | 0.060 |
| BARDAC ™ 2250J | 0.139 |  | 0.100 | 0 | 0 | 0 | 0 | 0 |
| SILWET ™ L-7600 | 0.100 | 0.100 | 0.175 | 0.100 | 0.100 | 0.100 | 0.100 | 0.100 |
| Citric Acid | 0.045 | 0.015 | 0.015 | 0.015 | 0.015 | 0.015 | 0.15 | 0.015 |
| Maleic Acid CAS 110-16-7 | 0 | 0.050 | 0.060 | 0.050 | 0.050 | 0.050 | 0.050 | 0.050 |
| ACES | 0.100 | 0 | 0 | 0 | 0 | 0 | 0 | 0 |
| Sodium Hydroxide | 0 | 0 | 0 | 0.020 | 0.020 | 0.020 | 0.020 | 0.020 |
| KORALONE ™ B-119 | 0 | 0.0150 | 0 | 0.015 | 0.015 | 0.015 | 0.015 | 0.015 |
| Ethanol | 3.000 | 3.000 | 3.000 | 3.000 | 3.000 | 3.000 | 3.000 | 3.000 |
| Deionized Water | 95.571 | 95.347 | 95.865 | 96.264 | 95.318 | 95.180 | 95.095 | 95.148 |
| Total |  |  | 100 |  | 100 | 100 | 100 | 100 |

The present invention encompasses the method of dispersing a mist of an effective amount of the composition for reducing malodor impression onto and into shoes wherein the shoes are not sprayed to saturation.

The present invention encompasses the method of dispersing a mist of an effective amount of the composition for reducing malodor impression onto shower curtains.

The present invention relates to the method of dispersing a mist of an effective amount of the composition for reducing malodor impression onto and/or into garbage cans and/or recycling bins.

The present invention relates to the method of dispersing a mist of an effective amount of the composition for reducing malodor impression into the air to neutralize malodor.

The present invention relates to the method of dispersing a mist of an effective amount of the composition for reducing malodor impression into and/or onto major household appliances including, but not limited to, refrigerators, freezers, washing machines, automatic dryers, ovens, microwave ovens, dishwashers, etc., to neutralize malodor.

Figure 1:
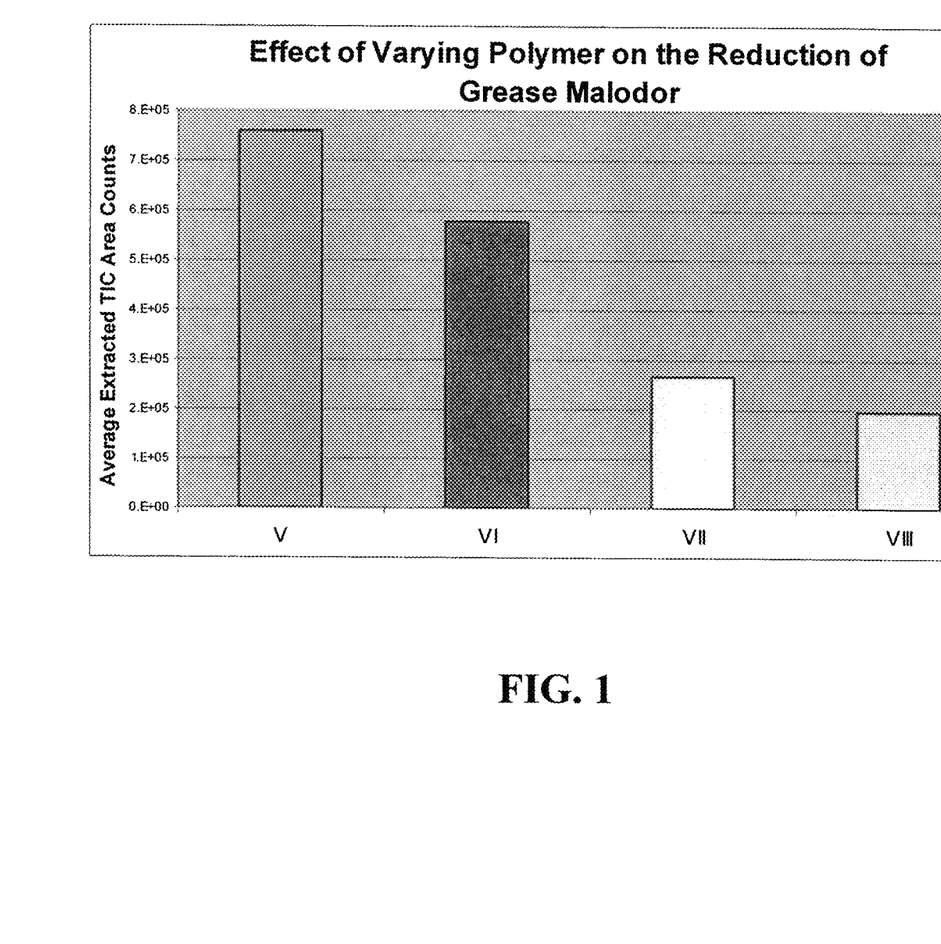
FIG. 1 is a bar graph showing the reduction of aldehydic malodors evaporating off fabrics treated with freshening compositions according to the present invention containing a malodor binding polymer in comparison to a freshening composition lacking such malodor binding polymer.

Formulations VI, VII, and VIII in Table 1 are prepared and compared to Control Formulation V, a composition containing no malodor binding polymer, for their effect on malodor. FIG. 1 shows that when including a malodor binding polymer in a freshening composition in accordance with the present invention, aldehydic malodor evaporating off the treated fabric decreases.

Fabric samples are infused with the malodor of interest. For grease infusion, place 8 ounces of grease in a Presto™ electric skillet and cover with the skillet lid. Place the skillet in a 30 gallon metal garbage can. Run the electric cord from the skillet through a 1.5 inch hole in the garbage can. Heat the skillet to 121° C. and allow it to equilibrate for 15 minutes. Remove the lid. Suspend 8 inch by 8 inch fabric swatches from the metal clips on a carousel in the garbage can lid. Measured from the bottom of the swatches, the distance to the top of the skillet is 8 inches. Place lid on garbage can and manually turn the carousel 15 rotations per minute for a period of 40 minutes. After infusion, spray the swatches with the respective freshening compositions that are to be tested. The spray for each swatch consists of two full strokes of the trigger sprayer bottle. The bottle is held 6 inches away from the fabric and the spray is centered on the fabric. Immediately after treatment, cut each swatch in half, roll, and place each into a 125 mL headspace vial. Seal the vials. Allow the vials to equilibrate for at least 2 hours at 100° C. and then analyze by sampling each vial using a PDMS SPME fiber and analyze by GC/MS. Malodor components, previously identified, are then tracked through all the samples. Data is compiled of total area count of the cumulative area counts of the individual peaks.

Microbe Reduction

Table 2 show non-limiting examples of freshening compositions according to the present invention.

TABLE 2

|  | IX (Control) | X |
|---|---|---|
| LUPASOL ™ WF CAS 9002-98-6 | 0 | 0.07 |
| Diethylene Glycol | 0.25 | 0.25 |
| Perfume mixture comprising aliphatic aldehydes | 0.02 (0.002 aldehydes) | 0.02 (0.002 aldehydes) |
| Hydroxypropyl Beta CD | 0.63 | 0.63 |
| BASOPHOR ™ ELH 60 | 0.15 | 0.15 |
| UNIQUAT ™ 2250 | 0 | 0 |
| BARDAC ™ 2250J | 0.5 | 0.5 |
| SILWET ™ L-7600 | 0.1 | 0.1 |
| Citric Acid | 0 | 0 |
| Maleic Acid CAS 110-16-7 | 0 | 0 |
| ACES | 0.1 | 0.1 |
| Sodium Hydroxide | 0.006 | 0.006 |
| KORALONE ™ B-119 | 0 | 0 |
| Ethanol | 3.000 | 3.000 |
| Deionized Water | 95.244 | 95.174 |
| Total | 100 | 100 |

Figure 2:
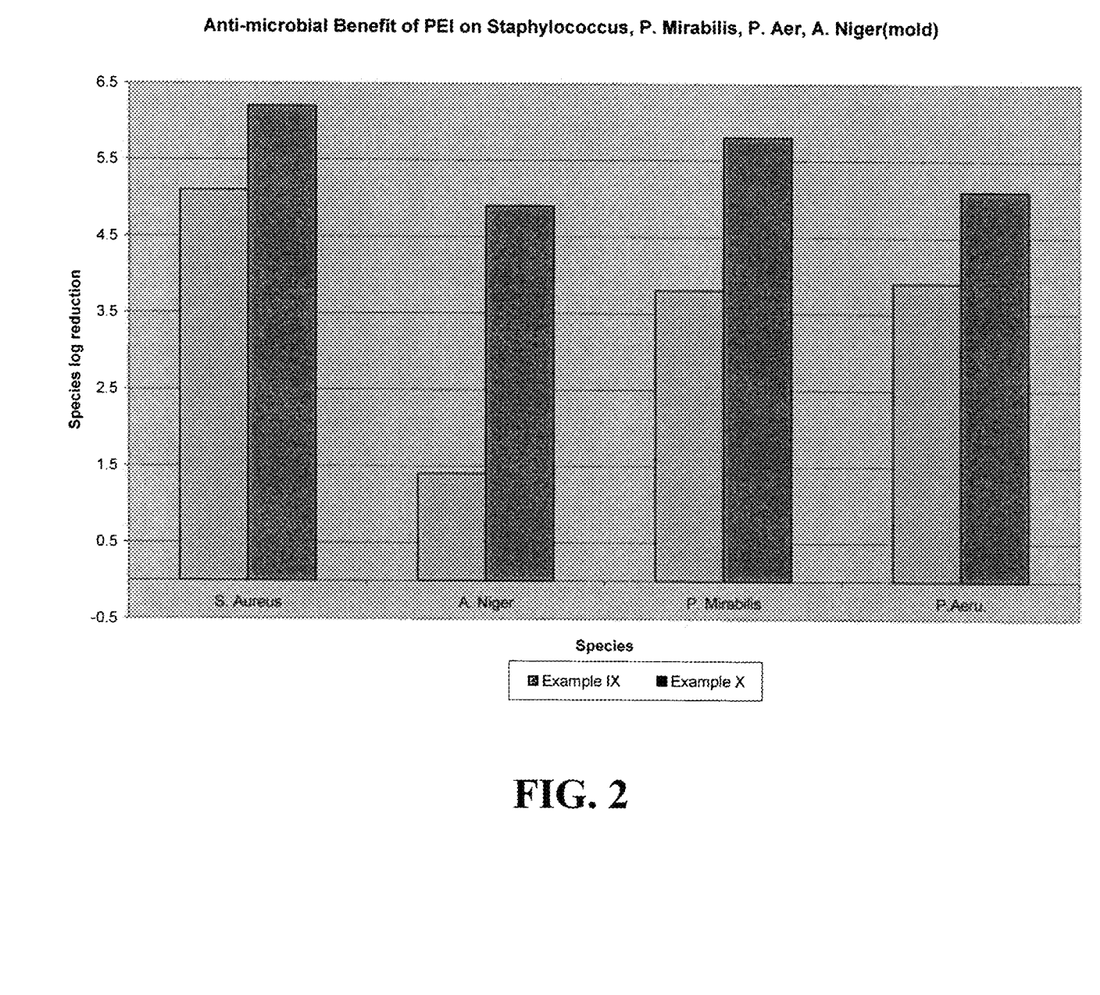
FIG. 2 is a bar graph showing microbe reduction with a freshening composition according to the present invention containing a malodor binding polymer in comparison to a freshening composition lacking such malodor binding polymer.

Formulation IX, the control formulation containing no malodor binding polymer, and Formulation X are compared for their effect on microbe reduction. FIG. 2 shows the results of formulations with and without PEIs when tested for non-residual fabric sanitizer efficacy against *Staphylococcus aureus* (ATCC 6538), *Aspergillus niger* (ATCC 6275), *Proteus mirabilis* (ATCC 7002) and *Pseudomonas aeruginosa* (ATCC 15442).

Formulation efficacy was assessed by employing a North American Bactericidal Fabric Spray Test Method that is a quantitative modification of the AOAC Germicidal Spray Products Test method (961.02). This method is a recognized test standard in accordance to U.S. EPA Pesticide Assessment Guidelines Subdivision G, Series 91-52(b)(1). The referenced AOAC method was applied to fabric surfaces. Fabric swatches (1.5 inch, 100% blue oxford cotton) as can be obtained from Testfabrics Inc. were treated with 2 fully depressed sprays of trigger sprayer bottle containing the respective formulation. A contact time between 10 to 30 minutes at ambient temperature was chosen as a conservative time estimate for sprayed fabric surfaces, as provided in Subdivision G, Series 91-1 (b)(4)(i). Any excess liquid is drained off and then transferred to a jar containing 20 ml neutralizer and/or growth promoting broth. The jar is mixed by vortexing, followed by sonication in a Branson Bransonic Ultrasonic Sonicator for 5 minutes. Within 30 minutes of neutralization, the jar is mixed for 2-3 seconds on a vortex type mixer and serially diluted. All the samples were incubated (48±4 hours) under the appropriate conditions and monitored for growth or no growth. Samples are plated and counted to determine mean log 10 reduction.

All percentages stated herein are by weight unless otherwise specified. It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross reference or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A freshening composition for reducing malodor comprising:
    about 0.01% to about 0.07%, by weight of said freshening composition, of a malodor binding polymer, wherein the malodor binding polymer is a homopolymeric polyethyleneimine having a molecular weight of about 25,000 Daltons and 15% to 80% primary amino groups;
    a malodor counteractant comprising at least one aliphatic aldehyde;
    from about 0.05% to about 1%, by weight of said composition, of surfactant; and
    an aqueous carrier;
    wherein said composition is essentially free of any material that would soil or stain fabric,
    wherein said composition comprises a pH of about 6 to about 8.

2. The composition of claim 1 wherein said at least one aliphatic aldehyde is present in the amount of about 0.001% to about 5% by total weight of said composition.

3. The composition of claim 2 wherein said at least one aliphatic aldehyde is selected from the group consisting of bourgeonal, citral, citronellyl oxyacetaldehyde, cymal, decyl aldehyde, helional, hexyl cinnamic aldehyde, lauric aldehyde, ligustral, lyral, melonal, methyl dihydro jasmonate, methyl nonyl acetaldehyde, methyl phenyl carbinyl acetate, nonyl aldehyde, 2" 6-nonadien-1-al, octyl aldehyde, oxane, P.T. bucinal, polysantol, rhubafuran, tripal, and mixtures thereof.

4. The composition of claim 1 wherein said at least one aliphatic aldehyde is present in the amount of about 0.001% to about 1% by total weight of said composition.

5. The composition of claim 1 wherein said composition further comprises a buffering agent selected from the group consisting of carboxylic acid, dicarboxcylic acid, N-(2-Acetamido)-2-aminoethanesulfonic acid, and mixtures thereof.

6. The composition of claim 1 wherein said composition further comprises maleic acid.

7. The composition of claim 1 wherein said composition is free of anionic surfactants.

8. The composition of claim 1 wherein said aqueous carrier is present in an amount of 90% to about 99.5%.

9. The freshening composition of claim 1, wherein the freshening composition reduces malodor on fabrics that are wetted with perspiration.

10. A method of reducing malodor comprising the steps of:
    a. providing the freshening composition of claim 1;
    b. dispersing an effective amount of said freshening composition on an inanimate surface or in the air.

11. An aqueous freshening composition for reducing malodor comprising:
    a homopolymeric polyethyleneimine having a molecular weight of about 25,000 Daltons and 15% to 80% primary amino groups;
    at least one aliphatic aldehyde;
    less than 1%, by weight of said composition, of a surfactant;
    a dicarboxylic acid to provide a pH of about 6 to about 8;
    and about 90% to about 99.5%, by weight of said composition, of an aqueous carrier;
    wherein said composition is essentially free of any material that would soil or stain fabric.

12. The aqueous freshening composition of claim 11, wherein the freshening composition reduces malodor on fabrics that are wetted with perspiration.

13. A freshening composition for reducing malodor comprising:
    about 0.01% to about 0.07%, by weight of said composition, of a malodor binding polymer, wherein the malodor binding polymer is a homopolymeric polyethyleneimine having a molecular weight of about 25,000 Daltons;
    about 0.001% to about 5%, by weight of said composition, of a malodor counteractant comprising at least one aliphatic aldehyde;
    less than 3%, by weight of said composition, of surfactant; and
    an aqueous carrier;
    wherein said composition is essentially free of any material that would soil or stain fabric,
    wherein said composition comprises a pH of about 6 to about 8.

14. The composition of claim 13 wherein said aqueous carrier is present in an amount of 90% to about 99.5%.

15. The freshening composition of claim 13, wherein the freshening composition reduces malodor on fabrics that are wetted with perspiration.

* * * * *